United States Patent [19]
Kang et al.

[11] Patent Number: 5,406,505
[45] Date of Patent: Apr. 11, 1995

[54] METHOD OF AND APPARATUS FOR MEASURING ENERGY GAP OF SEMICONDUCTOR

[75] Inventors: Seong-Jun Kang; Bo-Woo Kim; Yil-Sung Bae, all of Daejeon, Rep. of Korea

[73] Assignees: Electronic and Telecommunications Research Institute; Korea Telecommunication Authority, both of Rep. of Korea

[21] Appl. No.: 994,593

[22] Filed: Dec. 15, 1992

[51] Int. Cl.$^6$ ............................................. G01N 21/62
[52] U.S. Cl. .................................... 364/480; 356/372; 356/432; 364/481; 382/1; 382/8
[58] Field of Search ................. 356/372, 432; 364/480, 364/481; 382/1, 8

[56] References Cited

U.S. PATENT DOCUMENTS

| | | | |
|---|---|---|---|
| 4,761,073 | 8/1988 | Meltz et al. | 356/32 |
| 4,841,778 | 7/1989 | Butler et al. | 73/800 |
| 4,983,034 | 1/1991 | Spillman, Jr. | 356/32 |
| 5,020,379 | 6/1991 | Berthold et al. | 73/800 |
| 5,026,141 | 6/1991 | Griffiths | 250/227.14 |
| 5,064,270 | 11/1991 | Turpin et al. | 356/346 X |
| 5,255,070 | 10/1993 | Pollak et al. | 356/432 X |
| 5,260,772 | 11/1993 | Pollak et al. | 356/432 X |
| 5,270,797 | 12/1993 | Pollak et al. | 356/432 |

*Primary Examiner*—Edward R. Cosimano
*Attorney, Agent, or Firm*—Evenson, McKeown, Edwards & Lenahan

[57] ABSTRACT

A method and apparatus is disclosed for measuring an energy gap of a semiconductor material. The method contains the steps of analyzing a character of a reference semiconductor sample and setting an energy gap pixel value, estimating a transfer function between the pixel value, positioning the sample properly and imaging the spectrum to obtain a live image, storing the live image and scanning the respective pixel values along an x-axis of the image, sequentially comparing the respective pixel value and the energy gap pixel value, reading an x-coordinate of the pixel and converting the wavelength of the pixel to estimate the energy gap. The apparatus optically measures the energy gap and comprises a light source irradiating a light beam, a lens for focusing the light beam, a polychromator for irradiating the spectrum of light of the light beam to the sample, optical filters for evaluating a spectrum band of the polychromator into wavelength values, an image acquisition apparatus, an image signal processor, an energy gap detecting and displaying apparatus, and a computer for executing operation and control functions necessary to measure the energy gap by use of the image signal processor and the energy gap detecting and displaying apparatus.

3 Claims, 5 Drawing Sheets

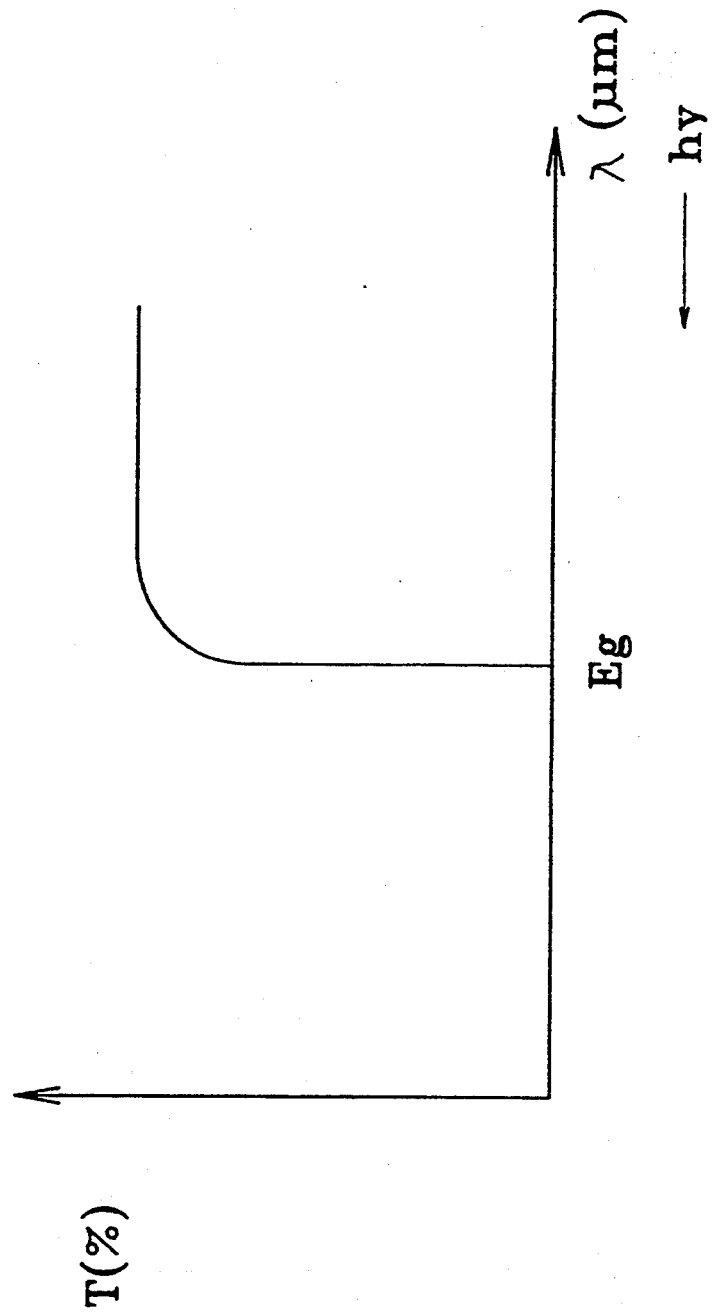

METHOD OF AND APPARATUS FOR MEASURING ENERGY GAP OF SEMICONDUCTOR

BACKGROUND AND SUMMARY OF THE INVENTION

The present invention relates to a method of and an apparatus for measuring an energy gap of a semiconductor material by using an image processing system.

A dimension of an energy gap serving as the most important electrical characteristic coefficient of a semiconductor material has been heretofore induced by using a spectrophotometer which continuously varies a wavelength of a light source and irradiates the light produced from the lightsource to a semiconductor sample so as to obtain an optical transimission spectrum on the basis of a theory which will be described later.

Such a spectrophotometer is known as the most important means for measuring a band structure of a semiconductor material.

Generally, when photons having an energy level '$h_v$' approximate to an energy gap Eg are irradiated to the semiconductor material, electrons are released from a conduction band to a valence band and, at this time, photons are absorbed in such a way of a light absorptive mechanism known so called as a fundamental absorption.

As noted above, from the photon induced electronic transition between bands of the material, the energy gap Eg of the semiconductor material can be easily measured.

The optical transmission in the semiconductor material can be expressed by a Dubrowskii formulation defined as belows. That is:

$$e^{-(\alpha d)} = [(A^2 + 2TA)^2 + 4T^2]^{\frac{1}{2}} - (A^2 + 2TA)/2T \quad (1)$$

where, $\alpha$ denotes an absorption coefficient, d denotes a thickness of a semiconductor sample and R denotes the amount of reflected light; and $A + T + R = 1$.

When the optical absorption is relatively large, the equation (1) can be expressed as the following MOSS equation. That is:

$$T = (1-R)^2 \exp^{-(\alpha d)} \quad (2)$$

Also, the absorption coefficient $\alpha$ in a fundamental absorption edge (band to band transition) can be expressed as the following equations with respect to a direct transition or indirect transition.

In the case of the direct transition as shown in FIG. 1(a)

$$\alpha = A(h_v - E_{gd})^{\frac{1}{2}}; \quad h_v > E_{gd} \quad (3)$$
$$= 0; \quad h_v \leq E_{gd}$$

in the case of the indirect transition as shown in FIG. 1(b)

$$\alpha = B(h_v - E_\theta - E_{gi})^2 + C(h_v + E_\theta - E_{gi})^2; \quad h_v > E_{gi} - E_\theta \quad (4)$$
$$= 0; \quad h_v \leq E_{gi} - E_\theta$$

where, Egd denotes a direct energy gap, Egi denotes an indirect energy gap and $E_\theta$ denotes a phonon energy gap. In the equations (4) the first term means that the phonons are emitted while the second term means that the phonons are absorbed. Accordingly, from the equations (3) and (4), the direct and indirect energy gaps Egd and Egi are induced by drawing tile relation of $\alpha^2 = f(h_v)$ and $\alpha^{\frac{1}{2}} = f(h_v)$ on respective graphs (a) and (b) as shown in FIG. 1. The value a is obtained from the transmitted light T and reflected light R under the given thickness of the semiconductor sample using the equation (1) or (2).

In the case of the direct transition of the equation (3), because the value $\alpha$ is set to zero under tile photon energy below the energy gap Eg, the transmission spectrum of a semiconductor material with no impurity is present arid the energy gap is shown in FIG. 2. From the spectrum shown in FIG. 2, the direct energy gap Egd can be obtained. That is, a start point of transmission in FIG. 2 indicates the energy gap Eg.

The method can be applied to most of compound semiconductor compounds because they have generally speaking the direct energy gap characteristics.

A goal underlying the present invention is to achieve a direct measurement of the energy gap with an infrared imaging system.

Accordingly, object of the present invention is to provide a method of and an apparatus for measuring an energy gap of semiconductor, in which a light source of a given band is irradiated to a semiconductor sample, and an image response is displayed on a monitor by applying a digital processing algorithm to obtain the images on the monitor.

To achieve the above object, according to one embodiment, the present invention contemplates a method of measuring an energy gap of a semiconductor, comprising:

analyzing character of a reference semiconductor sample and setting an energy gap pixel value;

estimating a transfer function between the pixel value comprising a transmission spectrum image and wavelengths of the corresponding pixels, positioning the sample properly and then obtaining a live image;

storing the live image and scanning the respective pixel values along a x-axis of the image;

sequentially comparing the respective pixel value and the energy gap pixel value, reading a x-coordinate of the pixel having a value coinciding with each other as the comparison value, and converting the wavelength of the pixel into a unit of eV to estimate the energy gap Eg.

According to another aspect, the present invention provides an apparatus for measuring an energy gap of a semiconductor, comprising:

a computer for executing all operation and control functions associated with measurement of the energy gap;

a lens for focusing the lighting beam irradiated from a light source;

a polychromator for irradiating the spectrum of the light to the sample;

optical filters for converting the polychromator's spectrum band into corresponding wavelength values.

an image acquisition apparatus for storing the image displayed on the monitor into memory an image signal processor for manipulating the digital data; and an energy gap detecting and displaying apparatus for defining a functional relation between the coordinate value and wavelength of the pixel.

With the present invention thus constructed, the light source of a given bandwidth is irradiated on the semiconductor sample and the response is imaged by the digital image processing system. Accordingly, the energy gap can be directly measured from the image displayed on the image processing system.

The above and other objects and advantages will be understood from the following description taken with reference to the accompanying drawings.

BRIEF DESCRIPTION OF THE DRAWINGS

FIG. 2 is a characteristic diagram of a transmission spectrum of a direct energy gap;

DETAILED DESCRIPTION OF THE INVENTION

Thereinafter, an embodiment of the present invention will be described in detail.

Referring to FIG. 3, an energy gap measuring principle according to the present invention is illustrated. A light source, for example, an infrared rays having a wavelength band λ, preferably 0.7-1.5 around an energy gap is irradiated to a semiconductor sample. The spectral characteristic of the light source transmitted through the sample is obtained in a form of an image by a digital image processing system. Accordingly, the value of energy gap can be directly read out from the image obtained by the image processing system.

As seen from FIG. 3, as an absorption coefficient α is increased, that is, when the absorption of the light is increased, a color of the image deepens. In other words, the image of the side of exhibits a dark color.

Figure 1B:
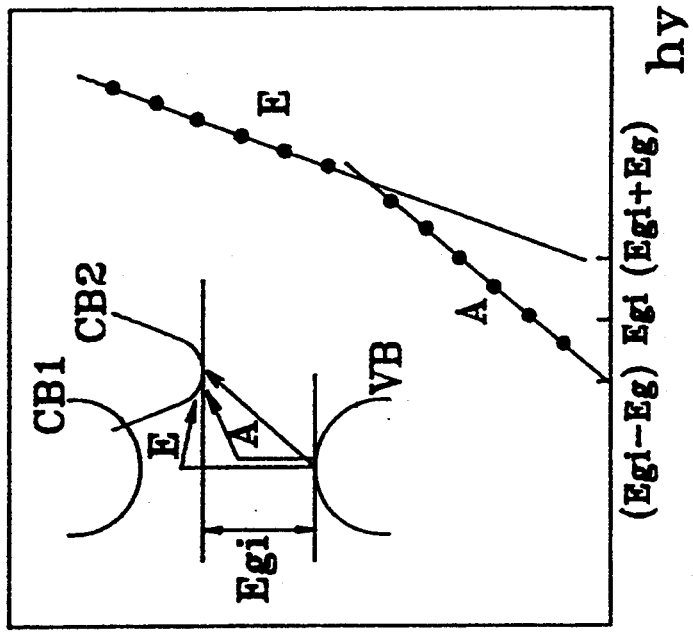
FIG. 1 is a view showing a known energy gap inducted on an α-graph, in which (a) is a graph showing a case of direct transition wherein CB represents the conduction band and VB represents the valence band, and (b) is a graph showing a case of an indirect transition wherein A is the phonon absorption $E_\theta$ and E is the phonon emission $E_\theta$.
Figure 1A:
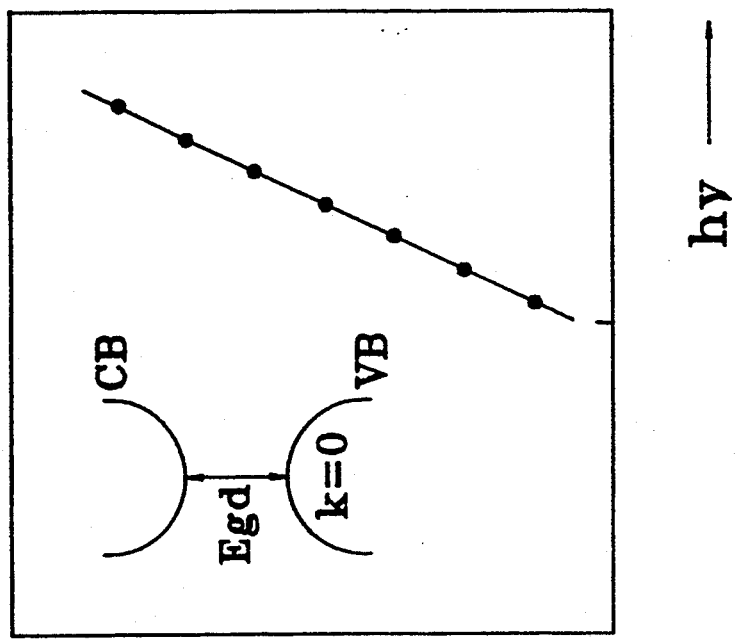
Figure 3A:
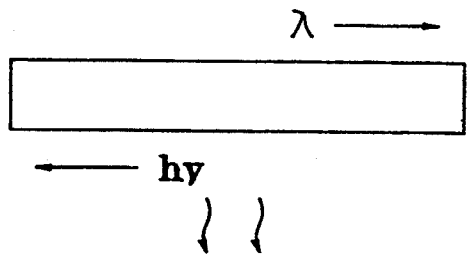
FIG. 3 is views illustrating a diagramatic construction of a principle which is employed to the present invention.
Figure 3B:
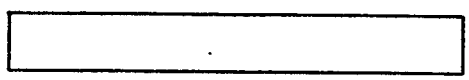
Figure 3C:
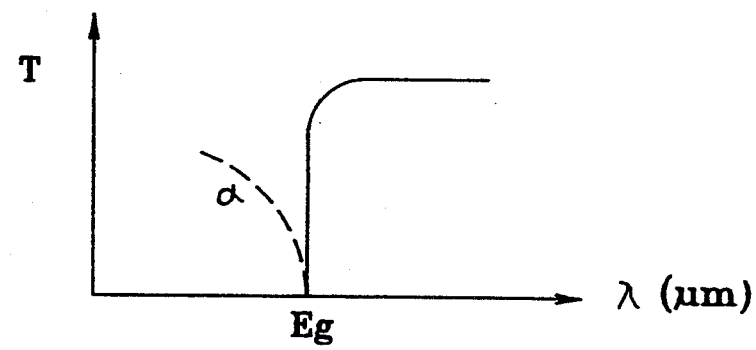
Figure 3D:
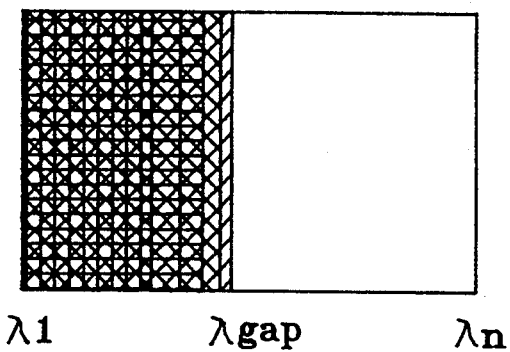
Figure 4:
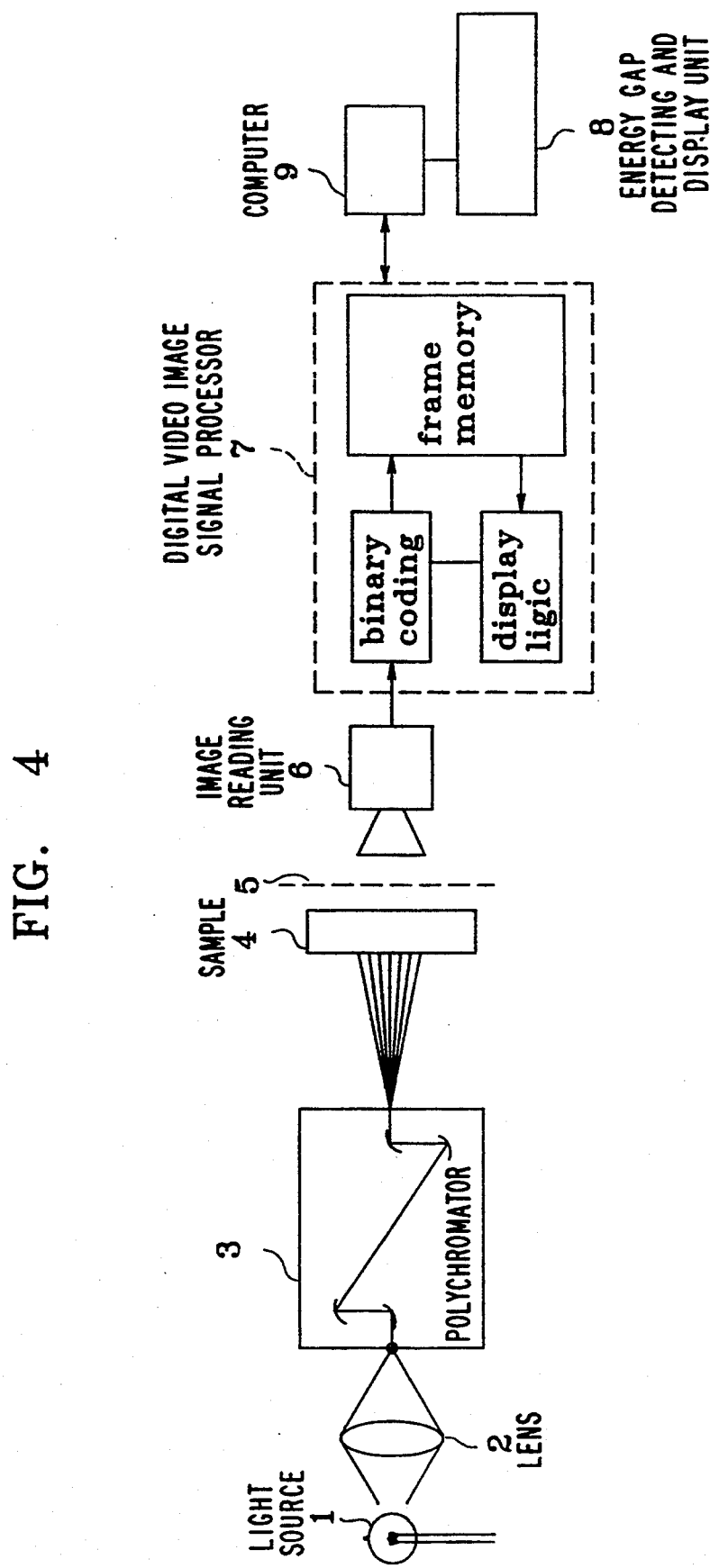
FIG. 4 is a block diagram of an apparatus according to an embodiment of the present invention; and, FIG. 5 is a flowchart illustrating a method of measuring the energy gap according to the present invention.

FIG. 4 is a block diagram of an energy gap measuring system according to an embodiment of the present invention. In the drawing, 1 denotes the light source, 2 is a lens for foucusing the light from the light source 1, 3 is a polychromator which is constructed by removing an output slit of a general-purpose monochromator, 5 is an optical filter which passes the light having different wavelength Α respectively, 6 is an image reading unit such as a silicon vidicon or charge coupled device (CCD), 7 is a digital video image signal processor, for example, a PCVISION FRAME GRABBER available from Imaging Technique Co., 8 is an energy gap detecting and displaying unit which defines the function relation between the pixel value of the image and the wavelength λ of the light, and 9 is an apparatus such as a personal computer for executing operation and control functions associated with the measuring of the energy gap.

The image signal processing unit 7 and the energy gap detecting and displaying unit 8 may be built in the computer 9.

Now, a method of setting a X-coordinate value λ of the image will be described.

First, a light beam having the constant wavelength band λ around the energy gap Eg is irradiated to tile sample 4. The spectrum of the light beam reflected from the sample 4 is imaged. In this case, it is required to define the actual wavelength value of the beam band.

More specifically, the relation (i.e., λ=f(x)) between the wavelength λ and the coordinate value X is estimated from the image on a monitor of the personal computer 9 or the display connected to the image signal processing unit 7. That is, the value (λ) can be estimated by obtaining the coordinate pixel values XP1, XP2 ... , XPn by several optical filters 5 each having a wavelength of λP1, λP2 ..., λPn arranged behind the sample 4 in FIG. 4. The optical filters pass only the light beam having a wavelength of λp and the spectrum images of the light beam passed are displayed on the monitor. The X-coordinate of the image displayed on the monitor indicates the wavelength λp.

Referring to FIG. 3, the sample 4 is irradiated with an infrared ray of a continuous band (substantially, wavelength of 0.7~1.5 μm) of the spectrum (the colors of the rainbow) having the different wavelengths as a lighting source.

In this case, the optical filters through which the specified wavelength of the light beam are passed, respectively are employed to understand the unknown wavelength values of the spectrum. Accordingly, as the optical filters are positioned between the sample and the image reading unit (in the order of red, orange, yellow, green, blue, indigo and violet as viewed from the left of the sample), an image of the wavelength of the light corresponding to the red color is displayed at the most leftside of the monitor while the image corresponding to the violet color is displayed at the most rightside of the monitor. Similarly, by positioning the optical filter having the wavelength corresponding to the green color between the sample and the image reading unit, an image corresponding to the green color is displayed on tile monitor. As a result, a X-coordinate value of the image displayed on the monitor corresponds to the wavelength of the green color. Therefore, the optical filters are employed for inducing the relation of λ=f(x).

If the wavelength in the spectrum is varied linearly, the relation [λ=f(x)] may be obtained by using two optical filters.

Now, such an energy gap (Eg) measuring method will be described with reference to FIG. 5.

Figure 5:
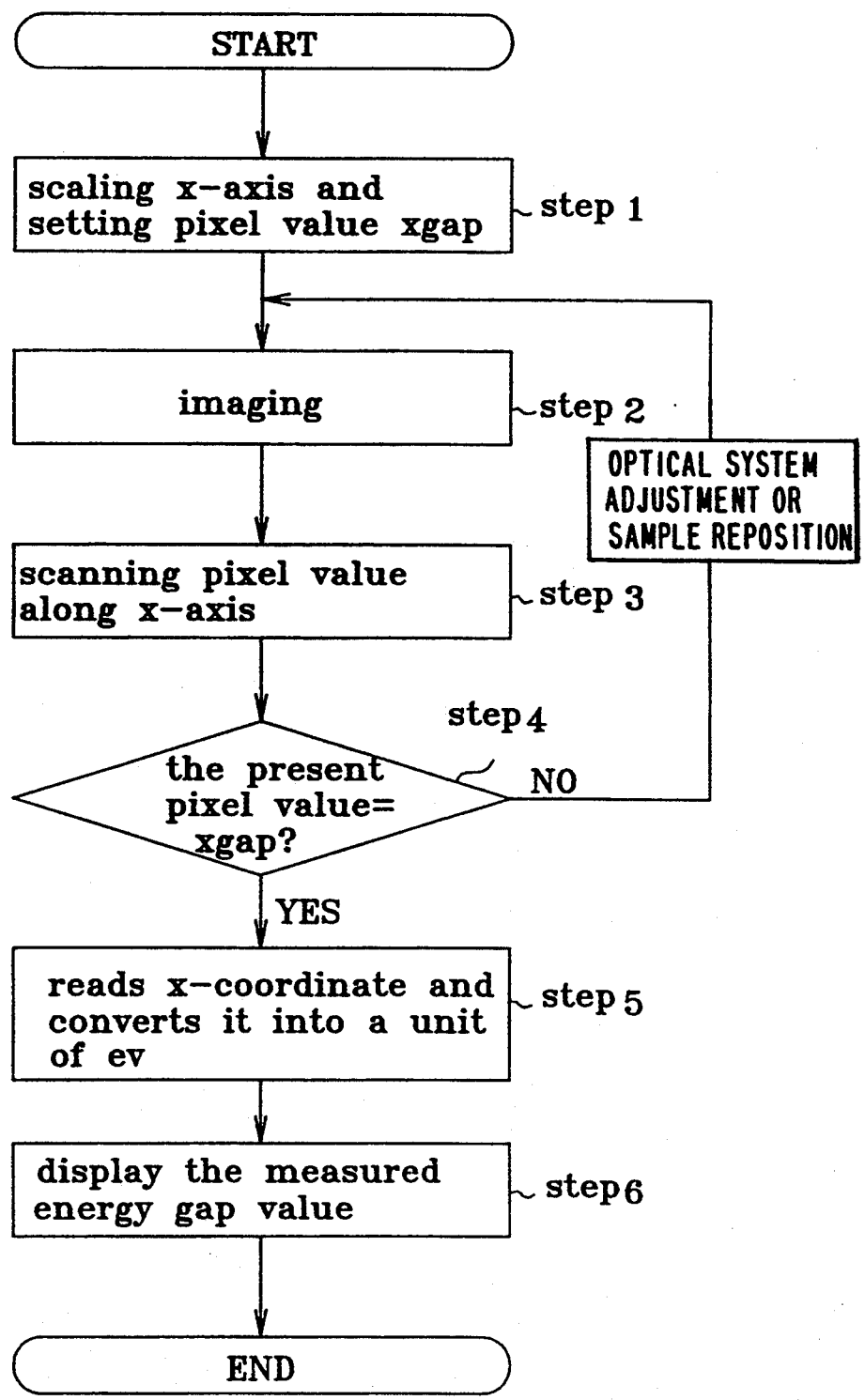

FIG. 5 shows a flowchart illustrating the energy gap measuring process. At a step 1 an energy gap pixel value Xgap is previously set in a program for energy gap (Eg) measure. Generally, a semiconductor retains an impurity of a certain content which forms an impurity level in the energy gap Eg and an impurity absorption is thus initiated by photon energy lower than tile energy gap Eg before the beginning of fundamental absorption.

For that reason, at the step 1 the pixel value Xgp corresponding to the energy gap Eg is previously set through the reference sample aleady analyzed in character in consideration of the immediately above described contents and the gray level of a background image according to the strength of the lighting source used in the optical system.

Next, at a step 2 a transfer function of $\lambda=f(x)$ in the optical system set at the step 1 through the energy gap detecting and displaying process is estimated by the optical filters and the sample 4 is positioned on the basis of the transfer function and an imaging process is carried out through the energy gap detecting and displaying unit 8. Then, a live image obtained by the image input unit 6 is stored in a frame memory of the image signal process. Consequently, the pixel values of the image on the monitor are scanned from the leftside toward the rightside (or, from the rightside toward the leftside) of the monitor at a step 3. Thus scanned pixel value X is compared with the energy gap pixel value Xgap, at a step 4. If the values coincede with each other, the X-coordinate of the corresponding pixel is read to estimate the value λ gap through the algorithms of $\lambda=f(x)$. Conversely, if the values do not coincide, the optical system is adjusted or the sample is repositioned to obtain an analyzable image. Thereinafter, tile term of 'gap' in the value 'λ gap' is varied in a unit of electron volt 'eV' from the relation of gap $(eV)=1.239/\lambda$ gap (μm), at a step 5.

The value of the energy gap Eg converted into a unit of eV is displayed on the monitor and the energy gap (Eg) measuring program is completed at a step 6.

As mentioned above, according to the present invention, the light beam having a given band irradiated to the sample is employed to obtain a response of the irradiation, instead of the existing spectrophotometer for continuously varying the wavelength of the light source and irradiating tile light source to the sample to obtain a transmission spectrum. The response is imaged and the energy gap is directly read from the imaged result through the digital image processing system having relatively a simplified structure. As a result, the energy gap can be correctly and quickly measured.

What is claimed is:

1. A method of measuring an energy gap of a semiconductor material, comprising the steps of:
   (a) irradiating a semiconductor sample with a light beam having a given wavelength band;
   (b) converting via optical filters, an x-coordinate of a transmission spectrum image into wavelength values;
   (c) analyzing a character of the semiconductor sample and setting an energy gap pixel value;
   (d) estimating a transfer function between the pixel value comprising the transmission spectrum image and wavelengths of corresponding pixels, positioning the sample properly and imaging the spectrum to obtain a live image;
   (e) storing the live image and scanning the respective pixel values along an x-axis of the image;
   (f) sequentially comparing the respective pixel value and the energy gap pixel value, reading a x-coordinate of the pixel having a value coinciding with each other as a comparison value; and
   (g) a pixel wavelength into a suite of eV to estimate the energy gap Eg.

2. A method according to claim 1, wherein the step (e) comprises previously setting the pixel value corresponding to the energy gap, scanning the respective pixel value of x-coordinate from leftside to rightside of the image or vice-versa, comparing the pixel values and reading the x-coordinate when the values coincide with each other as the energy gap.

3. An apparatus for optically measuring an energy gap of semiconductor material, comprising:
   a light source irradiating a light beam;
   a lens for focusing the light beam;
   a polychromator for irradiating the spectrum of light of the light beam to the sample;
   optical filters for evaluating a spectrum band of the polychromator into corresponding wavelength values;
   an image acquisition apparatus for storing an image displayed on a monitor into memory as digital image data;
   an image signal processor for manipulating the digital image data;
   an energy gap detecting and displaying apparatus for defining a functional relation between coordinate value and wavelength of a pixel; and
   a computer operatively associated with the image signal processor and the energy gap detecting and displaying apparatus for executing operation and control functions necessary to measure the energy gap.

* * * * *